(12) United States Patent
Karlsson et al.

(10) Patent No.: US 10,888,553 B2
(45) Date of Patent: Jan. 12, 2021

(54) USE OF NON-TRANSITION METAL COORDINATED DIPYRIDOXYL COMPOUNDS TO PREVENT AND TREAT CHEMOTHERAPY-INDUCED PSN

(71) Applicant: KARLSSON-TUNER INVEST AS, Trondheim (NO)

(72) Inventors: Jan-Olof G Karlsson, Trondheim (NO); Per Jynge, Hamar (NO); Rolf G G Andersson, Vikingstad (SE)

(73) Assignee: KARLSSON-TUNER INVEST AS, Trondhein (NO)

( * ) Notice: Subject to any disclaimer, the term of this patent is extended or adjusted under 35 U.S.C. 154(b) by 0 days.

(21) Appl. No.: 16/348,993

(22) PCT Filed: Nov. 13, 2017

(86) PCT No.: PCT/EP2017/078982
§ 371 (c)(1),
(2) Date: May 10, 2019

(87) PCT Pub. No.: WO2018/087347
PCT Pub. Date: May 17, 2018

(65) Prior Publication Data
US 2019/0282554 A1 Sep. 19, 2019

Related U.S. Application Data

(60) Provisional application No. 62/497,214, filed on Nov. 14, 2016.

(51) Int. Cl.
*A61K 31/444* (2006.01)
*A61K 31/555* (2006.01)
*A61K 45/06* (2006.01)
*A61P 25/02* (2006.01)
*A61K 31/675* (2006.01)

(52) U.S. Cl.
CPC .......... *A61K 31/444* (2013.01); *A61K 31/555* (2013.01); *A61K 31/675* (2013.01); *A61K 45/06* (2013.01); *A61P 25/02* (2018.01)

(58) Field of Classification Search
CPC .............. A61K 2300/00; A61K 31/444; A61K 31/555; A61K 31/675; A61K 15/06; A61P 25/02; A61P 35/00; A61P 43/00
See application file for complete search history.

(56) References Cited

U.S. PATENT DOCUMENTS

| | | | |
|---|---|---|---|
| 7,351,722 B2 | 4/2008 | Batteux et al. | |
| 8,377,969 B2 | 2/2013 | Karlsson et al. | |
| 9,187,509 B2 | 11/2015 | Karlsson et al. | |
| 2003/0166507 A1* | 9/2003 | Li | A61K 47/59 514/449 |

FOREIGN PATENT DOCUMENTS

| | | |
|---|---|---|
| EP | 1381364 B1 | 1/2004 |
| WO | 2009078794 A1 | 6/2009 |
| WO | 2013102806 A1 | 7/2013 |

OTHER PUBLICATIONS

PCT International Search Report and Written Opinion of the International Searching Authority dated Jan. 10, 2018 for corresponding PCT/EP2017/078982.
Jerome Alexandre et al.,"Improvement of the Therapeutic Index of Anticancer Drugs by the Superoxide Dismutase Mimic Mangafodipir", Journal of the National Cancer Institute, vol. 98, No. 4, Feb. 15, 1996.
Sassia Bedda, "Mangafodipir prevents liver injury induced by the acetaminophen in the mouse", Journal of Hepatology 39 (2003) 765-772.
Romain Coriat et al., "Treatment of oxaliplatin-induced peripheral neuropathy by travenous mangafodipir,The Journal of Clinical Investigation", vol. 124, No. 1, Jan. 2014.
Romain Coriat et al., "Mangafodipir Protects against Hepatic Ischemia Reperfusion Injury in Mice", PLoS ONE, Nov. 2011, vol. 6, Issue 11.
James H. Doroshow, "Redox Modulation of Chemotherapy-Induced Tumor Cell Killing and Normal Tissue Toxicity", Journal of the National Cancer Institute, vol. 98, No. 4, Feb. 15, 2006.

(Continued)

*Primary Examiner* — Erich A Leeser
(74) *Attorney, Agent, or Firm* — Renner, Otto Boisselle & Sklar, LLP (57) ABSTRACT

There is disclosed a platinum ion chelating dipyridoxyl compound according to Formula (I), or a pharmaceutically acceptable salt thereof, wherein the dipyridoxyl compound is uncoordinated or coordinated with a metal ion which is not a transition metal, for prevention or treatment of chemotherapy drug induced peripheral sensory neuropathy in a patient, wherein the chemotherapy drug comprises platinum ions. An example of such a chemotherapy drug is oxaliplatin. The drawbacks of previous metal complexed compounds containing manganese ions are eliminated. A more frequent use of the drug is possible since the problem in the prior art with accumulated manganese neurotoxicity is eliminated. The compounds can be administered both temporally and spatially separately from chemotherapy.

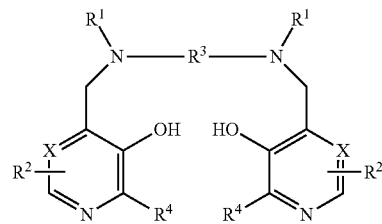

Formula I

11 Claims, 6 Drawing Sheets

(56) References Cited

OTHER PUBLICATIONS

Bengt Glimelius et al., "Persistent prevention of CIPN using calmangafodipir (PledOx): Results from a placebo-controlled randomized phase II study (PLIANT) in patients with metastatic colorectal cancer (mCRC)", Journal of Clinical Oncology; vol. 34, No. 15, suppl, May 1, 2016.
Jan Olof G. Karlsson et al., "Superior Therapeutic Index of Calmangafodipir in Comparison to Mangafodipir as a Chemotherapy Adjunct",Translational Oncology, vol. 5, No. 6, Dec. 2012, pp. 492-502.
Jan Olof G. Karlsson et al., "Calmangafodipir [Ca4Mn (DPDP)5], mangafodipir (MnDPDP) and Mn PLED with special reference to their SOD mimetic and therapeutic properties", Drug Discovery Today, vol. 20, No. 4, Apr. 2015.
Jan Olof G. Karlsson et al., "Mangafodipir a Selective Cytoprotectant—with Special Reference to Oxaliplatin and Its Association to Chemotherapy-Induced Peripheral Neuropathy (CIPN)1,2", Translational Oncology, vol. 10, No. xx, Month 2017, pp. 641-649.
Alexis Laurent, "Controlling Tumor Growth by Modulating Endogenous Production of Reactive Oxygen Species", Cancer Res 2005; 65: (3). Feb. 1, 2005.
K.G. Toft et al, "Metabolism and Pharmacokinetics of MnDPDP in Man", Acta Radiologica, 38 (1997) 677-689.
PCT/EP2017/078982; PCT International Preliminary Report on Patentability dated Oct. 30, 2018.
Aschner et al., "Manganese Dosimetry: Species Differences and Implications for Neurotoxicity", Critical Reviews in Toxicology, 35, pp. 1-32, 2005.
Blanusa et al., "Chelators as Antidotes of Metal Toxicity: Therapeutic and Experimental Aspects", Current Medicinal Chemistry, 2005, vol. 12, pp. 2771-2794.
Brurok et al., "Manganese Dipyridoxyl Diphosphate: MRI Contrast Agent with Antioxidative and Cardioprotective Properties?" Biochemical and Biophysical Research Communications, 254, pp. 768-772, Dec. 21, 1988.
Ferlay et al., "Estimates of the cancer incidence and mortality in Europe in 2006", Annals of Oncology, vol. 18, No. 3, pp. 581-592, vol. 18, No. 3, Mar. 2007.

Gamelin et al., "Prevention of Oxaliplatin-Related Neurotoxicity by Calcium and Magnesium Infusions: A Retrospective Study of 161 Patients Receiving Oxaliplatin Combined with 5-Fluorouracil and Leucovorin for Advanced Colorectal Cancer", Clinical Cancer Research, vol. 10, pp. 4055-4061, Jun. 15, 2004.
Higa & Sypult, "Molecular Biology and Clinical Mitigation of Cancer Treatment-Induced Neuropathy", Clinical Medicine Insights: Oncology 2016: 10 , pp. 27-34.
Karlsson et al., "First Clinical Experience with the Magnetic Resonance Imaging Contrast Agent and Superoxide Dismutase Mimetic Mangafodipir as an Adjunct in Cancer Chemotherapy—A Translational Study 1,2", Translational Oncology, vol. 5, No. 1, Feb. 2012, pp. 32-38.
Karlsson et al., "Cardioprotective Effects of the MR Contrast Agent MnDPDP and Its Metabolite MnPLED Upon Reperfusion of the Ischemic Porcine Myocardium", Acta Radiologica, 42, pp. 540-547, 2001.
Kurz et al., "Effects of MnDPDP and ICRF-187 on Doxorubicin-Induced Cardiotoxicity and Anticancer Activity 1", Translational Oncology, vol. 5, No. 4, Aug. 2012, pp. 252-259.
Loprinzi et al, "Phase III Randomized, Placebo-Controlled, Double-Blind Study of Intravenous Calcium and Magnesium to Prevent Oxaliplatin-Induced Sensory Neurotoxicity (N08CB/Alliance)", Journal of Clinical Oncology, vol. 32, No. 10, Apr. 1, 2014.
McWhinney et al., "Platinum neurotoxicity pharmacogenetics", Mol Cancer Ther 2009; (8) (1). Jan. 2009.
O' Neil et al., "Innovations in Chemotherapy for Metastatic Colorectal Cancer: An Update of Recent Clinical Trials", The Oncologist, 2008; 13: pp. 1074-1083.
Pachman et al., "The search for treatments to reduce chemotherapy-induced peripheral neuropathy", The Journal of Clinical Investigation; vol. 124, No. 1, Jan. 2014, pp. 72-74.
Shord et al., "Oxaliplatin Biotransformation and Pharmacokinetics: A Pilot Study to Determine the Possible Relationship to Neurotoxicity", Anticancer Research 22: pp. 2301-2310, 2002.
Takagi et al., "Evaluation of indexes of in vivo manganese status and the optimal intravenous dose for adult patients undergoing home parenteral nutrition 1-3", American Journal of Clinical Nutrition 2002: 75: pp. 112-118, 2002.
Yri et al., "Mangafodipir as a cytoprotective adjunct to chemotherapy—a case report", Acta Oncologica, 2009.

* cited by examiner

24-hour Recovery of Platinum in Urine (% of given dose)

| Saline + oxaliplatin | Mangafodipir + oxaliplatin | Fodipir + oxaliplatin |
|---|---|---|
| 31.3 | 33.8 | 43.4 |

FIG. 3

Formula I

USE OF NON-TRANSITION METAL COORDINATED DIPYRIDOXYL COMPOUNDS TO PREVENT AND TREAT CHEMOTHERAPY-INDUCED PSN

This application is a national phase of International Application No. PCT/EP2017/078982 filed Nov. 13, 2017 and published in the English language, which claims priority to U.S. Provisional Application No. 62/497,214 filed Nov. 14, 2016, both of which are hereby incorporated by reference.

FIELD OF INVENTION

The present invention is directed to non-transition metal coordinated dipyridoxyl compounds, for example N,N'-bis-(pyridoxyl-5-phosphate)-ethylenediamine-N,N'-diacetic acid (DPDP or fodipir) or other related compounds (such as PyrdidoxyL EthylDiamine derivatives; PLED-derivatives) for use in treatment of a chemotherapy drug injury, in particular peripheral sensory neuropathy (PSN) induced by platinum ion containing chemotherapy drugs such as oxaliplatin.

BACKGROUND OF THE INVENTION

Oxaliplatin in combination with 5-fluorouracil (5-FU) is a potent chemotherapy drug to treat colorectal cancer (CRC) but the clinical use of oxaliplatin is compromised by severe peripheral sensory neuropathy (PSN). The exact mechanism behind PSN is poorly understood but it is related to retention of $Pt^{2+}$ in the body and subsequent protein binding. Oxaliplatin-associated PSN differs from cisplatin-associated PSN. Both cause a peripheral stocking-glove neuropathy that worsens with the cumulative dose (Loprinzi et al., J Clin Oncol 2014; 32: 997-1005). Oxaliplatin but not cisplatin is associated with an acute neuropathic problem that generally occurs after each oxaliplatin dose and often resolves within a few days. Although the acute form can be quite bothersome, it is the chronic PSN that is the general dose-limiting problem and the main cause of complete discontinuation of oxaliplatin treatment. The chronic neuropathy is characterized by bilaterally symmetrical sensory symptoms (e.g., numbness, tingling, and pain) appearing in the feet and hands. It is generally accepted that it is retention of $Pt^{2+}$ in dorsal root ganglion that causes PSN.

Human exposure to a number of metals such as lead, cadmium, mercury, manganese, aluminum, iron, copper, thallium, arsenic, chromium, nickel and platinum may lead to toxic effects, which differ for each metal. In the case of platinum (Pt), and as for many other metals, the metallic uncharged (non-ionic) form is not linked to any major adverse health effects. However, soluble metal compounds such as metal ions are much more toxic, in particular coordination complexes containing $Pt^{2+}$, such as the chemotherapy drug oxaliplatin. The tumoricidal activity of Pt-containing drugs depends on $Pt^{2+}$ crosslinking of DNA strands. $Pt(II)-Cl_2$, one of many metabolites of oxaliplatin, is the only metabolite of oxaliplatin that is able to crosslink DNA. However, it is less than 3% of oxaliplatin that is converted into the active metabolite $Pt(II)-Cl_2$ (Shord et al. Anticancer Res. 2002; 22:2301-2309). Although it is possible that $Pt(II)-Cl_2$ may contribute to some DNA crosslinking in non-dividing peripheral nerve cells, such an effect is expected to be rather limited. It is hence reasonable to anticipate that it is the non-active metabolites that cause oxalipaltin-induced PSN (Shord et al., 2002), through binding of $Pt^{2+}$ to intracellular proteins in nerve cells.

A chelating agent is a molecule that forms a complex with a metal ion. The chelating molecule has electrons available to form bonds with a positively charged transition metal ion. The main goal of chelation treatment is to transform the toxic metal complex with biological ligands into a new, non-toxic complex between the toxic metal ion and chelator, which can be readily excreted from the organism. These goals, however, are not easy to fulfill but there are ligands clinical available for treatment of for instance iron- and copper-overload (Blanusa et al., Current Medicinal Chemistry 2005; 12:2771-2794).

Oxaliplatin features a square planar platinum(II; $Pt^{2+}$) center coordinated to the bidentate ligand 1,2-diaminocyclohexane and a bidentate oxalate group. The main route of excretion of oxaliplatin-derived platinum is through the kidneys. However, a large proportion accumulates in the body for a considerable amount of time. From literature and the discussion below, it seems reasonable to propose that toxic side-effects, e.g., neurotoxicity, caused by oxaliplatin, are mainly due to retention of Pt-metabolites, other than the tumoricidal $Pt(II)-Cl_2$ one, and subsequent binding of $Pt^{2+}$ to proteins in normal cells.

There is no routinely recommended chelation therapy for either oxaliplatin or cisplatin, although limited human data suggest DDTC (sodium diethylcarbodtithioate) as possibly effective treatment in patients receiving high-dose cisplatin therapy, in order to alleviate toxic side effects, without significantly affecting cisplatin's tumoricidal properties (Blanusa et al., 2005). However, as discussed below, both the toxic and the therapeutic profile of oxaliplatin differs from that of cisplatin. This difference is most probably due to oxaliplatin being a far more lipophilic compound than cisplatin, which has a considerable impact on how these compounds distributes in the body after administration. The much more lipophilic oxaliplatin disappear from the extracellular compartment much rapidly than cisplatin, and Pt-derived oxaliplatin is hence more difficult to reach with a renal excretable chelator, i.e., a hydrophilic one. This difference apparently governs the possibility to treat the toxicities of these two compounds.

The expression "chelating therapy" in association with oxaliplatin is a frequently used expression among oncologists. However, the semantic meaning of the expression in this context is strange and has nothing in common with "chelating therapy" in the sense of administering chelating compounds to treat metal intoxication. French investigators initially proposed that calcium and magnesium infusion would be helpful for preventing oxaliplatin-induced neuropathy; it was hypothesized that the reason for the difference between the neurotoxicity of oxaliplatin and cisplatin was that oxalate was metabolized from oxaliplatin, and oxalate was known to chelate calcium and magnesium, elements involved in the function of ion channels in nerve membranes. Thus, it was believed that calcium and/or magnesium might prevent or ameliorate oxaliplatin induced neurotoxicity (Gamelin et al. Clin Cancer Res. 2004; 10:4055-4061). This hypothesis defined the expression "chelating therapy" in the oncological field. Although this hypothesis, from a theoretical standpoint, is more or less unlikely, this particular infusion was in common use for more than 10 years. It was eventually demonstrated in a phase III clinical trial (N08CB/Alliance) that calcium and magnesium infusion did not prevent oxaliplatin-associated PSN (Loprinzi et al. 2014)."

No other treatments have been proven effective against oxaliplatin-induced PSN (Pachman et al. J Clin Invest 2014; 124:72-74). Recent clinical results suggest that mangafodipir (MnDPDP) or calmangafodipir [MnCa$_4$(DPDP)$_5$] may be used as an effective therapy against this condition. One example is the interpretation of data in U.S. Pat. No. 9,187,509 suggesting that mangafodipir may protect against peripheral sensory neuropathy (column 3 top). According to prior art, these compounds or their metabolites protects against oxaliplatin-induced PNS via a catalytic activity which depends on the transition metal manganese. In this sense, mangafodipir and calmangafodipir mimics the mitochondrial superoxide dismutase (MnSOD), the world fastest enzyme, by dismutating superoxide ($O_2^-$) into $H_2O_2$ and $H_2O$. No aerobic creature survives without a functional SOD. Both native MnSOD and MnSOD mimetics depend on manganese ($Mn^{3+}/Mn^{2+}$) that catalyzes a one-electron oxidation and a one-electron reduction during the dismutating action. However, manganese may cause a cumulative form of brain toxicity that limits repeated use MnSOD mimetics. Theoretical assumptions suggest that it should be possible to safely administer up to 15 repeated doses of calmangafodipir but for mangafodipir this number is less (Karlsson et al. Transl Oncol 2017; 10:641-649). The manganese in those complexes may result in a number of undesired effects including manganese-induced neurotoxicity.

Cancer of the colon or rectum (colorectal adenocarcinomas; CRC) is the second most common cancer in US and Europe. About half of the colorectal cancer patients will ultimately die of the disease, corresponding annually to about 50,000 people in US (O'Neil & Goldberg. Oncologist. 2008; 13; 1074-1083) and 200,000 people in Europe (Ferlay et al. Ann Oncol. 2006; 18:581-592).

The chance to survive from colorectal cancer (CRC) depends on the stage of the disease, generally being high in patients with a cancer confined to the primary site (stage I and II) and low in advanced metastatic disease (stage IV) (O'Neil & Goldberg, 2008). In about ⅓ of the diagnosed colorectal cancers the disease is locally advanced to one or more lymph nodes (stage III). Postoperative adjuvant chemotherapy in stage III colon cancer patients, for many years with 5-fluorouracil (5-FU) alternatively capecitabine alone, and now in combination with oxaliplatin, has increased survival substantially in this group from about 50% to more than 70%). The other Pt(II)-containing drugs on the market, i.e., cisplatin and carboplatin (alone or in combination with other chemotherapy drugs), do not demonstrate efficacy against CRC.

Oxaliplatin plus 5-FU (FOLFOX) or oxaliplatin plus capecitabine (XELOX) is administered in cycles of two or three weeks, respectively. In the adjuvant setting, patients are treated with 12 FOLFOX cycles or 9 XELOX cycles. Because of severe adverse events, particular PSN, caused by oxaliplatin dose reductions are common. In the palliative setting, patients are treated as long as treatment is beneficial.

However, the efficacy of oxaliplatin in combination with 5-FU is severely compromised because of a substantial risk of toxicity, in particularly oxaliplatin-induced peripheral sensory neuropathy (PSN). Toxicity represents in more than half of the patients an intolerable burden and causes dose reductions, delays or, in worth case, complete discontinuations of therapy. PSN is the main cause to complete discontinuation of oxaliplatin. Residual (chronic) PSN is a feared consequence of using oxaliplatin. Numerous methods to prevent and to treat PNS have so far been proven unsuccessful (Pachman et al., J Clin Invest. 2014; 124:72-74).

Oxaliplatin, a third-generation platinum agent, is considered one of the two most important new drugs used in the treatment of CRC (Higa & Sypult. Clinical Medicine Insight: Oncology. 2016; 10:27-34). Despite the clinical impact and attendant enthusiasm for this agent, the applicability of oxaliplatin is limited, in large part, by PSN. Importantly, neurotoxicity, and not tumor progression, is the most frequent reason that forces patients to forego further therapy with this agent. Because the approved use of oxaliplatin has, for the first time in over 50 years, improved overall survival in patients with colorectal cancer (CRC), innovative research with respect to oxaliplatin-induced PNS is highly appreciated (Higa & Sypult, 2016). Importantly, clinical data indicate an apparent lack of correlation between Pt-induced neurotoxicity and tumor response (McWhinney et al. Mol Cancer Ther. 2009; 8:10-16), suggesting that neurotoxicity may be prevented without altering tumoricidal efficacy.

A recent publication by Coriat and co-workers (J Clin Invest. 2014; 124:262-272) and a prior case report by Yri et al. (Acta Oncol. 2009; 48:633-635), however, describe that co-treatment with i.v. mangafodipir may reduce oxaliplatin-induced PSN in CRC patients. Importantly, the data from the Coriat et al. study suggest that mangafodipir not only prevents but surprisingly also cures ongoing PSN. These authors demonstrated that patients with pre-existing oxaliplatin-induced PSN (grade 2 or worth on a 1-3 scale) improved after combined oxaliplatin and mangafodipir treatment. Because the severity of oxaliplatin-induced PNS correlates with the cumulative dose, continued treatment with oxaliplatin alone is expected to aggravate PNS. Both publications suggest that the manganese superoxide dismutase (MnSOD) mimetic activity of mangafodipir (Brurok et al. Biochem Biophys Res Commun. 1999; 254:768-772; Bedda et al. (Hepatol. 2003; 39:765-772) protects against oxaliplatin-induced PSN, in a similar manner as MnPLED-derivatives protects against myocardial injuries caused by ischemia-reperfusion (Karlsson et al. Acta Radiol. 2001; 42:540-547) and doxorubicin (Kurz et al. Transl Oncol. 2012; 5:252-259), respectively, chemotherapy-induced myelosuppression (Alexandre et al. J Natl Cancer Inst. 2006; 98:236-244; Karlsson et al. Transl Oncol. 2012A; 5:32-38; Karlsson et al. Transl Oncol. 2012B; 5:492-502), and paracetamol (acetaminophen)-induced liver failure (Bedda et al., 2003).

An externally administered MnSOD mimetic is, however, expected to result in a transient increase in SOD activity, mainly governed by the elimination of the MnPLED-derivatives from the body (i.e., MnDPDP, MnDPMP and MnPLED). Pharmacokinetic data from human volunteers, as described by Toft et al. (Acta Radiol 1997; 38:677-689), suggests that very little or no DPDP/DPMP/PLED-bound $Mn^{2-}$ is left in the body 10 hours after administration of MnDPDP. On theoretical grounds such a compound is hence only expected to have a preventive efficacy when administered close to the oxaliplatin administration and not a curative efficacy on an already established PSN.

Co-administration of MnPLED-derivatives does not interfere negatively with the anticancer effect of chemotherapy. In opposite, MnPLED-derivatives have an anticancer effect of their own (Laurent et al. Cancer Res. 2005; 65:948-956; Alexandre et al. J Natl Cancer Inst. 2006; 98:236-244; Karlsson et al., 2012B). The anticancer effect of mangafodipir (and other MnPLED-derivatives) is not an inherent property of the intact manganese complex but of fodipir (or its metabolites, DPMP and PLED) alone (U.S. Pat. Nos. 8,377,969; 9,187,509; Karlsson et al., 2012B), whereas, for instance, its cardioprotective effect depends on the SOD mimetic activity (see Karlsson et al. Drug Discovery Today. 2015; 20:411-421).

Manganese (Mn) is an essential as well as potentially neurotoxic metal (Aschner et al., Crit Rev Toxicol. 2005; 35:1-32). It has been known for many years that, under conditions of chronic exposure to manganese, a syndrome of extrapyramidal dysfunction similar to Parkinson's disease (PD) may occur. Mn neurotoxicity is well established in patients receiving parenteral nutrition, where doses exceeding 1 µmol/day (corresponding to 14 nmol/kg in a 70-kilogram person) are associated with elevated risk for developing neurological symptoms. Mn accumulates in the brain with an elimination half-life exceeding 50 days. The threshold for cumulative intravenous Mn toxicity in monkeys is well defined (5 mg/kg), corresponding to ~100 µmol/kg.

Neurological symptoms correlate well with accumulation of Mn in the basal ganglia, seen as hyperintensity on T1-weighted MRI (Takagi et al. Am J Clin Nutr. 2002; 35:112-118). The patient in the aforementioned case report (Yri et al., 2009) received 10 µmol/kg mangafodipir in 14 of 15 chemotherapy cycles, resulting in an accumulated dose of 140 µmol/kg. Brain MRI after 14 cycles with mangafodipir showed increased T1-weighted signal intensity in the basal ganglia. This patient showed PD-like neurological symptoms.

Coriat et al., 2014 reported that the mean plasma Mn content increased from 11.8±5.5 nM to 19.8±4.3 nM, all within normal reference values, after eight cycles with 5 µmol/kg mangafodipir co-treatment (corresponding to an accumulated dose of 40 µmol/kg). However, plasma Mn is considered as a weak predictor of Mn neurotoxicity (Takagi et al., 2002). A much more reliable predictor is brain T1-weighted MRI. MRI was not conducted in the study by Coriat et al. Two of the inventors of the present invention (Karlsson and Jynge) together with Judy Aschner and Michael Aschner (two renowned experts in the field of manganese neurotoxicity) have commented on the serious problem with neurotoxicity in relation to the Coriat paper in an e-letter 2014 (https://content.the-jci.org/eletters/view/68730) to Journal of Clinical Investigation.

$Mn^{2+}$ bound to fodipir is likely non-neurotoxic, but $Mn^{2+}$ released from fodipir may pass the blood-brain-barrier, causing neurotoxicity. About 80% of the $Mn^{2+}$ content of mangafodipir is released upon intravenous administration (Toft et al., 1997). It is possible to stabilize mangafodipir by replacing 4/5 of its $Mn^{2+}$ content with $Ca^{2+}$, resulting in a compound known as calmangafodipir $[Ca_4Mn(DPDP)_5]$ (U.S. Pat. No. 9,187,509; Karlsson et al., 2012B). At equivalent intravenous Mn doses, calmangafodipir causes considerably less Mn release and retention in the rat brain and is significantly more efficacious than mangafodipir to protect mice against chemotherapy-induced leukocytopenia. Although manganese retention (and brain retention) is reduced to about 50%, it still occurs and restricts the use of calmangafodipir. Thus it is still desired to provide a treatment of PSN without these drawbacks.

Calmangafodipir is at present in clinical phase II in CRC patients, stage IV (ClinicalTrials.gov Identifier: NCT01619423). Preliminary results from this study presented so far (see Karlsson et al., 2017) suggest that calmangafodipir may ameliorate oxalipaltin-induced PSN. Other data presented by PledPharma AB, suggest a more pronounced effect of the compound on the chronic form of PSN than on the acute form. These data apparently also support a curative rather than a preventive effect of calmangafodipir. Standard chemotherapy with 5-FU plus oxaliplatin (FOLFOX) in stage III CRC patients involves 12 consecutive cycles. From a risk-benefit perspective it seems reasonable to include calmangafodipir co-administration in each of these cycles, in order to lower the incidence of PSN. For more frequent use accumulated Mn neurotoxicity will most probably represent an insurmountable obstacle. It is thus a problem in the prior art to be able to treat PSN during frequent use of oxaliplatin and other similar drugs comprising platinum ions.

SUMMARY OF THE INVENTION

It is an object of the present invention to alleviate at least some of the disadvantages of the prior art and to provide an improved method for preventing or treating peripheral sensory neuropathy caused by a chemotherapy drug comprising platinum ions.

The present invention provides non-transition metal coordinated compounds for use to treat chemotherapy induced drug injuries from platinum ion containing chemotherapy drugs such as oxaliplatin-induced PSN.

In a first aspect there is provided a platinum ion chelating dipyridoxyl compound according to Formula I, or a pharmaceutically acceptable salt thereof, wherein the dipyridoxyl compound is uncoordinated or coordinated with a metal ion which is not a transition metal, for prevention or treatment of chemotherapy drug induced peripheral sensory neuropathy in a patient, wherein the chemotherapy drug comprises platinum ions, Formula I wherein
X represents CH or N,
each $R^1$ independently represents hydrogen or —$CH_2COR^5$;
$R^5$ represents hydroxy, optionally hydroxylated alkoxy, amino or alkylamido;
each $R^2$ independently represents $ZYR^6$ wherein Z represents a bond or a $C_{1-3}$ alkylene or oxoalkylene group, optionally substituted by $R^7$;
Y represents a bond, an oxygen atom or $NR^6$;
$R^6$ is a hydrogen atom, $COOR^8$, alkyl, alkenyl, cycloalkyl, aryl or aralkyl group, optionally substituted by one or more groups selected from $COOR^8$, $CONR^8_2$, $NR^8_2$, $OR^8$, =$NR^8$, =O, OP(O) $(OR^8)R^7$ and $OSO_3M$;
$R^7$ is hydroxy, optionally hydroxylated, optionally alkoxylated alkyl or aminoalkyl group;
$R^8$ is a hydrogen atom or an optionally hydroxylated, optionally alkoxylated alkyl group;
M is a hydrogen atom or one equivalent of a physiologically tolerable cation;
$R^3$ represents a $C_{1-8}$ alkylene, a 1,2-cykloalkylene, or a 1,2-arylene group, optionally substituted with $R^7$; and
each $R^4$ independently represents hydrogen or $C_{1-3}$ alkyl.

In a second aspect there is provided a method for the prevention or treatment of a chemotherapy drug induced peripheral sensory neuropathy in a patient, wherein the chemotherapy drug comprises platinum ions, the method comprising administering to the patient an effective amount of a platinum ion chelating dipyridoxyl compound according to Formula I as described above, or a pharmaceutically acceptable salt thereof, wherein the dipyridoxyl compound is uncoordinated or coordinated with a metal ion which is not a transition metal.

In a third aspect there is provided use of platinum ion chelating dipyridoxyl compound according to Formula I as described above or a pharmaceutically acceptable salt thereof, wherein the dipyridoxyl compound is uncoordinated or coordinated with a metal ion which is not a transition metal for the manufacture of a medicament for prevention or treatment of chemotherapy drug induced peripheral sensory neuropathy in a patient, wherein the chemotherapy drug comprises platinum ions.

In a fourth aspect there is provided use of platinum ion chelating dipyridoxyl compound according to Formula I as described above, or a pharmaceutically acceptable salt thereof, wherein the dipyridoxyl compound is uncoordinated or coordinated with a metal ion which is not a transition metal, for prevention or treatment of chemotherapy drug induced peripheral sensory neuropathy in a patient, wherein the chemotherapy drug comprises platinum ions.

Advantages of the invention include the possibility of efficiently reducing the drawbacks of chemotherapy drugs comprising platinum ions, such as oxaliplatin. Further the drawbacks of previous compounds containing manganese ions is eliminated.

A further advantage is that a more frequent use of the drug is possible since the drawbacks of the previous treatments with accumulated manganese neurotoxicity are eliminated. Thus a far more frequent administration is possible compared to manganese containing compounds such as for instance mangafodipir and calmangafodipir.

Yet another advantage is that the compounds according to Formula I can be administered both temporally and spatially separated from chemotherapy.

BRIEF DESCRIPTION OF THE DRAWINGS

The invention is described with reference to the following drawings in which.

DETAILED DESCRIPTION OF THE INVENTION

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

As used herein the terms "alkyl" and "alkylene" include straight-chained and branched, saturated and unsaturated hydrocarbons. The term "1,2-cykloalkylene" includes both cis and trans cycloalkylene groups and alkyl substituted cycloalkylene groups having from 5-8 carbon atoms. The term "1,2-arylene" includes phenyl and naphthyl groups and alkyl substituted derivatives thereof having from 6 to 10 carbon atoms. Unless otherwise specified, any alkyl, alkylene or alkenyl moiety may conveniently contain from 1 to 20, more specifically 1-8, more specifically 1-6, and even more specifically, 1-4 carbon atoms. Cycloalkyl moieties may conveniently contain 3-18 ring atoms, specifically 5-12 ring atoms, and even more specifically 5-8 ring atoms. Aryl moieties comprising phenyl or naphthyl groups are preferred. As aralkyl groups, phenyl $C_{1-8}$ alkyl, especially benzyl, are preferred. Where groups may optionally be substituted by hydroxyl groups, this may be monosubstitution or polysubstitution and, in the case of polysubstitution, alkoxy and/or hydroxyl substituents may be carried by alkoxy substituents.

As used herein the term "transition metal" denotes an element whose atom has a partially filled d sub-shell. Examples include but are not limited to Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, and Hg. A "non-transition metal" denotes a metal which is not a transition metal. As used herein the term "metal" includes both the ions as well as the elemental metal, unless the context clearly dictates otherwise.

As used herein the term "chelating" denotes the property of a compound to form chelate complexes, also referred to as coordination complexes. Examples include a platinum ion chelating dipyridoxyl compound which has the ability to form a chelate complex, (i.e. a coordination complex) with the compound and a platinum ion. A platinum chelating compound is likely to be able to chelate also other metal ions, for instance the dipyridoxyl compounds of the invention are able to chelate platinum ions as well as other ions.

"Platinum ion chelating dipyridoxyl compound" thus means that the dipyridoxyl compound has the ability to chelate with a platinum ion and form a chelate (i.e. complex), however it does not mean the compound is limited to form chelates with only platinum, on the contrary the compound is able to form chelates with other ions as well. The affinity of the metal ion to the compound may vary between different ions.

As used herein the term "coordinated" denotes that a compound and a metal ion form a coordination complex. Such a coordination complex is also referred to as a chelate complex. In the case of the compounds according to the invention, if the compound it coordinated, then one metal ion is coordinated with one molecule. The dipyridoxyl compound of the invention is uncoordinated or coordinated with a metal ion to form a coordination complex or a chelate complex.

In a first aspect there is provided a platinum ion chelating dipyridoxyl compound according to Formula I, or a pharmaceutically acceptable salt thereof, wherein the dipyridoxyl compound is uncoordinated or coordinated with a metal ion which is not a transition metal, for prevention or treatment of chemotherapy drug induced peripheral sensory neuropathy in a patient, wherein the chemotherapy drug comprises platinum ions, Formula I wherein
X represents CH or N,
each R$^1$ independently represents hydrogen or —CH$_2$COR$^5$;
R$^5$ represents hydroxy, optionally hydroxylated alkoxy, amino or alkylamido;
each R$^2$ independently represents ZYR$^6$ wherein Z represents a bond or a C$_{1-3}$ alkylene or oxoalkylene group, optionally substituted by R$^7$;
Y represents a bond, an oxygen atom or NR$^6$;
R$^6$ is a hydrogen atom, COOR$^8$, alkyl, alkenyl, cycloalkyl, aryl or aralkyl group, optionally substituted by one or more groups selected from COOR$^8$, CONR$^8{}_2$, NR$^8{}_2$, OR$^8$, =NR$^8$, =O, OP(O) (OR$^8$)R$^7$ and OSO$_3$M;
R$^7$ is hydroxy, optionally hydroxylated, optionally alkoxylated alkyl or aminoalkyl group;
R$^8$ is a hydrogen atom or an optionally hydroxylated, optionally alkoxylated alkyl group;
M is a hydrogen atom or one equivalent of a physiologically tolerable cation;
R$^3$ represents a C$_{1-8}$ alkylene, a 1,2-cykloalkylene, or a 1,2-arylene group, optionally substituted with R$^7$; and each R$^4$ independently represents hydrogen or C$_{1-3}$ alkyl.

It is conceived that the dipyridoxyl compound is either uncoordinated or coordinated with a metal ion which is not a transition metal. Thus in one embodiment the dipyridoxyl compound is uncoordinated i.e. not coordinated with any metal ion. In another embodiment the dipyridoxyl compound is coordinated with a metal ion which is not a transition metal ion. If the dipyridoxyl compound is coordinated, then one dipyridoxyl compound is typically coordinated with one metal ion.

In one embodiment the chemotherapy drug comprises oxaliplatin. Combinations of chemotherapy drugs are also encompassed such as a combination of 5-FU and oxaliplatin.

In one embodiment the metal which is not a transition metal comprises at least one selected from the group consisting of calcium and magnesium. It is important to note that the limitation non-transition metal or metal which is not a transition metal excludes metals such as manganese. In one embodiment the metal which is not a transition metal is calcium. In one embodiment the metal which is not a transition metal is magnesium. In one embodiment the metal which is not a transition metal is a mixture of calcium and magnesium so that some complexes comprise a calcium ion and some complexes comprise a magnesium ion. Calcium and magnesium are suitable metal ions since their affinity to the chelating compound according to Formula I are suitable. Their affinity is anticipated to be lower than that of platinum ions, although the affinity for platinum ions to these compounds is not known. Nevertheless, when platinum ions are present the equilibrium is supposed to be shifted so that a considerable amount of coordinated calcium and/or magnesium ions are replaced by platinum ions. At the same time calcium and magnesium ions are not likely to cause any notable negative effects at the relevant concentrations. Contrary, coordinated calcium may in fact protect against (non-coordinated) fodipir-induced reduction in the extracellular concentration of free calcium, upon rapid intravenous administration. Since the heart is absolutely dependent on extracellular calcium for its blood pumping activity, rapid reduction in the extracellular content of free calcium may induce acute heart failure. This can easily be solved by making use of calcium-coordinated fodipir (or metabolites) (U.S. Pat. No. 9,187,509). In one embodiment the metal which is not a transition metal is a metal which is known not to cause any notable adverse effects.

In one embodiment the compound is administered at 1 to 100 μmol/kg body weight of the compound. In an alternative embodiment the compound is administered at 5 to 50 μmol/kg body weight of the compound. In yet an alternative embodiment the compound is administered at 5 to 30 μmol/kg body weight of the compound. In one embodiment the compound is administered orally. In another embodiment the compound is administered intravenously. In one embodiment the concentration of the compound in a solution for injection is in the interval 1-100 mM.

The compound according to Formula I, e.g. Fodipir or other PLED-derivatives is suitably administered in a pharmaceutical composition. Optionally, the pharmaceutical compositions comprising the compound may include one or more physiologically acceptable carriers and/or excipients, in a manner well-known to those skilled in the art. In one embodiment, the compound may for example be suspended or dissolved in a liquid medium, optionally with the addition of pharmaceutically acceptable excipients. Suitable excipients for the pharmaceutical compositions include any conventional pharmaceutical or veterinary formulation excipients, including, but not limited to, stabilizers, antioxidants, osmolality adjusting agents, buffers, pH adjusting agents, binders, fillers, and the like. The pharmaceutical compositions may be in a form suitable for administration, including both parenteral and enteral administration. In a specific embodiment, the composition is in a form suitable for example injection or infusion. Thus, pharmaceutical compositions comprising the compound of the present invention may be in a conventional pharmaceutical administration form such as a tablet, capsule, powder, solution, suspension, dispersion, syrup, suppository, aerosol, ointment, plaster, or the like.

Such compositions may be administered by various routes, for example orally, transdermally, rectally, intrathecally, topically or by means of inhalation or injection, in particular subcutaneous, intramuscular, intraperitoneal or intravascular injection. Other routes of administration may be used as well, including intratympanic and intranasal, and routes which increase the effectiveness, the bioavailability or the tolerance of the products are preferred. The most appropriate route can be chosen by those skilled in the art according to the particular formulation which is used.

The present use of mangafodipir (Karlsson et al., 2012A; Coriat et al., 2014) or calmangafodipir (ClinicalTrials.gov Identifier: NCT01619423) as an adjunct to FOLFOX is by parenteral administration. FOLFOX is administered as an intravenous infusion in hospital, co-treatment with intravenous mangafodipir or calmangafodipir is therefore of little problem. However, it would be of a great advantage of a perorally active formulation when it comes to treatment temporally and spatially separated from chemotherapy. This would allow treatment out of hospital. From a theoretic starting point, an enteric coated $Ca^{2+}$-coordinated PLED would be preferred. This is a relatively small (Mw 518) and uncharged compound around neutral pH (Rocklage et al. Inorg Chem. 1988; 27:3530-3534). The low pH in the stomach will cause $Ca^{2+}$ to dissociate from PLED, and this will result in increased charge of PLED which in turn will affect the gastrointestinal absorption of the compound negatively. This could be fixed by enteric coating resistant to gastric acid but that starts to dissolve when it reaches the small intestine, making use of methods known among those skilled in the art. The gastrointestinal tract is lined with epithelial cells. Drugs must pass or permeate through these cells in order to be absorbed into the circulatory system. Indirect evidence shows that MnPLED has to readily pass cell membranes of the heart in order to protect the heart against ischemia-reperfusion injuries (Karlsson et al., 2001) and injuries caused by doxorubicin (Kurz et al., 2012). This actually suggests that MnPLED as well as CaPLED will be absorbed in the intestine. The size and the gross charge of these two compounds are more or less identical. The gastrointestinal absorption of uncoated MnPLED after having been instilled into the stomach of rats is described in U.S. Pat. No. 6,310,051. As expected the absorption of intact MnPLED was more or less absent and although PLED was detected in blood plasma 5 minutes to 2 hours post administration of 100 µmol/kg, the concentration was not higher than 1 µM. However, the bioavailability of an enteric coated formulation of CaPLED, for reasons given above, is expected to be good.

In one embodiment, the treatment method according to the invention comprises administering about 1 to 100 µmol/kg body weight of the compound. In more specific embodiments, the treatment method according to the invention comprises administering about 5 to 50 µmol/kg, or about 5 to 30 µmol/kg, body weight of the compound. A peroral route of administration will probably demand a higher dose than the parenteral route, because of lower bioavailability of the former. A skilled person is in the light of this description able to adapt the dose.

In one embodiment the treatment with the compound according to formula I is carried out at the same time as the treatment with the chemotherapy drug. In another embodiment the treatment with the compound according to formula I is carried out partially at the same time as the treatment with the chemotherapy drug. In yet another embodiment the treatment with the compound according to formula I is carried out before the treatment with the chemotherapy drug. In another embodiment the treatment with the compound according to formula I is carried out after the treatment with the chemotherapy drug. In yet another embodiment the treatment is carried out according to any possible combination of the above embodiments. Assuming that oxaliplatin possibly together with other chemotherapy drugs is given during at least one 14-day cycle, then in one non-limiting embodiment the compound according to Formula I is administered from day 6-10.

In one embodiment $R^5$ is hydroxy, $C_{1-8}$ alkoxy, ethylene glycol, glycerol, amino or $C_{1-8}$ alkylamido; Z is a bond or a group selected from $CH_2$, $(CH_2)_2$, CO, $CH_2CO$, $CH_2CH_2CO$ and $CH_2COCH_2$; Y is a bond; $R^6$ is a mono- or poly(hydroxy or alkoxylated) alkyl group or of the formula $OP(O)(OR^8)R^7$; and $R^7$ is hydroxy, or an unsubstituted alkyl or aminoalkyl group.

In one embodiment $R^3$ is ethylene and each group $R^1$ represents $—CH_2COR^5$ in which $R^5$ is hydroxy.

In one embodiment the compound of Formula I is one selected from the group consisting of N,N'-bis-(pyridoxal-5-phosphate)-ethylenediamine-N,N'-diacetic acid (DPDP; fodipir), N,N'-dipyridoxyl ethylenediamine-N,N'-diacetic acid (PLED), and a pharmaceutically acceptable salt thereof. In yet an embodiment the compound of Formula I is N,N'-bis-(pyridoxal-5-phosphate)-ethylenediamine-N,N'-diacetic acid (DPDP; fodipir) or a pharmaceutically acceptable salt thereof.

In a second aspect there is provided a method for the prevention or treatment of a chemotherapy drug induced peripheral sensory neuropathy in a patient, wherein the chemotherapy drug comprises platinum ions, the method comprising administering to the patient an effective amount of A platinum ion chelating dipyridoxyl compound according to Formula I, or a pharmaceutically acceptable salt thereof, wherein the dipyridoxyl compound is uncoordinated or coordinated with a metal ion which is not a transition metal, Formula I wherein
X represents CH or N,
each $R^1$ independently represents hydrogen or $—CH_2COR^5$;
$R^5$ represents hydroxy, optionally hydroxylated alkoxy, amino or alkylamido;

each $R^2$ independently represents $ZYR^6$ wherein Z represents a bond or a $C_{1-3}$ alkylene or oxoalkylene group, optionally substituted by $R^7$;

Y represents a bond, an oxygen atom or $NR^6$;

$R^6$ is a hydrogen atom, $COOR^8$, alkyl, alkenyl, cycloalkyl, aryl or aralkyl group, optionally substituted by one or more groups selected from $COOR^8$, $CONR^8{}_2$, $NR^8{}_2$, $OR^8$, $=NR^8$, $=O$, $OP(O)(OR^8)R^7$ and $OSO_3M$;

$R^7$ is hydroxy, optionally hydroxylated, optionally alkoxylated alkyl or aminoalkyl group;

$R^8$ is a hydrogen atom or an optionally hydroxylated, optionally alkoxylated alkyl group;

M is a hydrogen atom or one equivalent of a physiologically tolerable cation;

$R^3$ represents a $C_{1-8}$ alkylene, a 1,2-cykloalkylene, or a 1,2-arylene group, optionally substituted with $R^7$; and each $R^4$ independently represents hydrogen or $C_{1-3}$ alkyl.

In one embodiment of the method the chemotherapy drug comprises oxaliplatin.

In one embodiment of the method the metal which is not a transition metal comprises at least one selected from the group consisting of calcium and magnesium.

In one embodiment of the method the method comprises administering about 1 to 100 μmol/kg body weight of the compound. In another embodiment of the method the method comprises administering about 5 to 50 μmol/kg body weight of the compound. In yet another embodiment of the method the method comprises administering about 5 to 30 μmol/kg body weight of the compound.

In one embodiment of the method $R^5$ is hydroxy, $C_{1-8}$ alkoxy, ethylene glycol, glycerol, amino or $C_{1-8}$ alkylamido; Z is a bond or a group selected from $CH_2$, $(CH_2)_2$, CO, $CH_2CO$, $CH_2CH_2CO$ and $CH_2COCH_2$; Y is a bond; $R^6$ is a mono- or poly(hydroxy or alkoxylated) alkyl group or of the formula $OP(O)(OR^8)R^7$; and $R^7$ is hydroxy, or an unsubstituted alkyl or aminoalkyl group.

In one embodiment of the method $R^3$ is ethylene and each group $R^1$ represents $-CH_2COR^5$ in which $R^5$ is hydroxy.

In one embodiment of the method the compound of Formula I is one selected from the group consisting of N,N'-bis-(pyridoxal-5-phosphate)-ethylenediamine-N,N'-diacetic acid (DPDP; fodipir), N,N'-dipyridoxyl ethylenediamine-N,N'-diacetic acid (PLED), and a pharmaceutically acceptable salt thereof. In another embodiment of the method the method In one embodiment of the method the compound of Formula I is N,N'-bis-(pyridoxal-5-phosphate)-ethylenediamine-N,N'-diacetic acid (DPDP; fodipir) or a pharmaceutically acceptable salt thereof.

In one embodiment of the method the chemotherapy drug comprises oxaliplatin.

In a third aspect there is provided use of platinum ion chelating dipyridoxyl compound according to Formula I, or a pharmaceutically acceptable salt thereof, wherein the dipyridoxyl compound is uncoordinated or coordinated with a metal ion which is not a transition metal, wherein X represents CH or N, each $R^1$ independently represents hydrogen or $-CH_2COR^5$;

$R^5$ represents hydroxy, optionally hydroxylated alkoxy, amino or alkylamido;

each $R^2$ independently represents $ZYR^6$ wherein Z represents a bond or a $C_{1-3}$ alkylene or oxoalkylene group, optionally substituted by $R^7$;

Y represents a bond, an oxygen atom or $NR^6$;

$R^6$ is a hydrogen atom, $COOR^8$, alkyl, alkenyl, cycloalkyl, aryl or aralkyl group, optionally substituted by one or more groups selected from $COOR^8$, $CONR^8{}_2$, $NR^8{}_2$, $OR^8$, $=NR^8$, $=O$, $OP(O)(OR^8)R^7$ and $OSO_3M$;

$R^7$ is hydroxy, optionally hydroxylated, optionally alkoxylated alkyl or aminoalkyl group;

$R^8$ is a hydrogen atom or an optionally hydroxylated, optionally alkoxylated alkyl group;

M is a hydrogen atom or one equivalent of a physiologically tolerable cation;

$R^3$ represents a $C_{1-8}$ alkylene, a 1,2-cykloalkylene, or a 1,2-arylene group, optionally substituted with $R^7$; and each $R^4$ independently represents hydrogen or $C_{1-3}$ alkyl, for the manufacture of a medicament for prevention or treatment of chemotherapy drug induced peripheral sensory neuropathy in a patient, wherein the chemotherapy drug comprises platinum ions.

In a fourth aspect there is provided use of platinum ion chelating dipyridoxyl compound according to Formula I, or a pharmaceutically acceptable salt thereof, wherein the dipyridoxyl compound is uncoordinated or coordinated with a metal ion which is not a transition metal, wherein X represents CH or N, each $R^1$ independently represents hydrogen or $-CH_2COR^5$;

$R^5$ represents hydroxy, optionally hydroxylated alkoxy, amino or alkylamido;

each $R^2$ independently represents $ZYR^6$ wherein Z represents a bond or a $C_{1-3}$ alkylene or oxoalkylene group, optionally substituted by $R^7$;

Y represents a bond, an oxygen atom or $NR^6$;

$R^6$ is a hydrogen atom, $COOR^8$, alkyl, alkenyl, cycloalkyl, aryl or aralkyl group, optionally substituted by one or more groups selected from $COOR^8$, $CONR^8{}_2$, $NR^8{}_2$, $OR^8$, $=NR^8$, $=O$, $OP(O)(OR^8)R^7$ and $OSO_3M$;

$R^7$ is hydroxy, optionally hydroxylated, optionally alkoxylated alkyl or aminoalkyl group;

$R^8$ is a hydrogen atom or an optionally hydroxylated, optionally alkoxylated alkyl group;

M is a hydrogen atom or one equivalent of a physiologically tolerable cation;

$R^3$ represents a $C_{1-8}$ alkylene, a 1,2-cykloalkylene, or a 1,2-arylene group, optionally substituted with $R^7$; and each $R^4$ independently represents hydrogen or $C_{1-3}$ alkyl, for prevention or treatment of chemotherapy drug induced peripheral sensory neuropathy in a patient, wherein the chemotherapy drug comprises platinum ions.

Each of the different embodiments described above can be freely combined with all other embodiments. Embodiments of the different aspects can be freely combined, for instance an embodiment of the compound can be combined with an embodiment of the method.

The compound of Formula I may have the same or different $R^2$ groups on the two pyridyl rings and these may be attached at the same or different ring positions. In a specific embodiment, the substitution is at the 5- and 6-positions, or more specifically, the 6-position, para to the hydroxyl group. In a specific embodiment, the $R^2$ groups are identical and identically located, and more specifically are in the 6,6'-positions.

In yet more specific embodiments, each $R^6$ is a mono- or poly(hydroxy or alkoxylated) alkyl group or a group of the formula $OP(O)(OR^8)R^7$.

In one embodiment, $R^5$ is hydroxy, $C_{1-8}$ alkoxy, ethylene glycol, glycerol, amino or $C_{1-8}$ alkylamido; Z is a bond or a group selected from $CH_2$, $(CH_2)_2$, CO, $CH_2CO$, $CH_2CH_2CO$ and $CH_2COCH_2$; Y is a bond; $R^6$ is a mono- or poly(hydroxy or alkoxylated) alkyl group or of the formula $OP(O)(OR^8)R^7$; and R7 is hydroxy, or an unsubstituted alkyl or aminoalkyl group. In a more specific embodiment, $R^3$ is ethylene and each group $R^1$ represents —$CH_2COR^5$ in which $R^5$ is hydroxy. In a further embodiment, the compound of Formula I is N,N'-bis-(pyridoxal-5-phosphate)-ethylenediamine-N,N'-diacetic acid (DPDP), or a pharmaceutically acceptable salt thereof. In still further embodiments, the compound is N,N'-bis-(pyridoxal-5-phosphate)-ethylenediamine-N,N'-diacetic acid, or a salt thereof.

Figure 6:
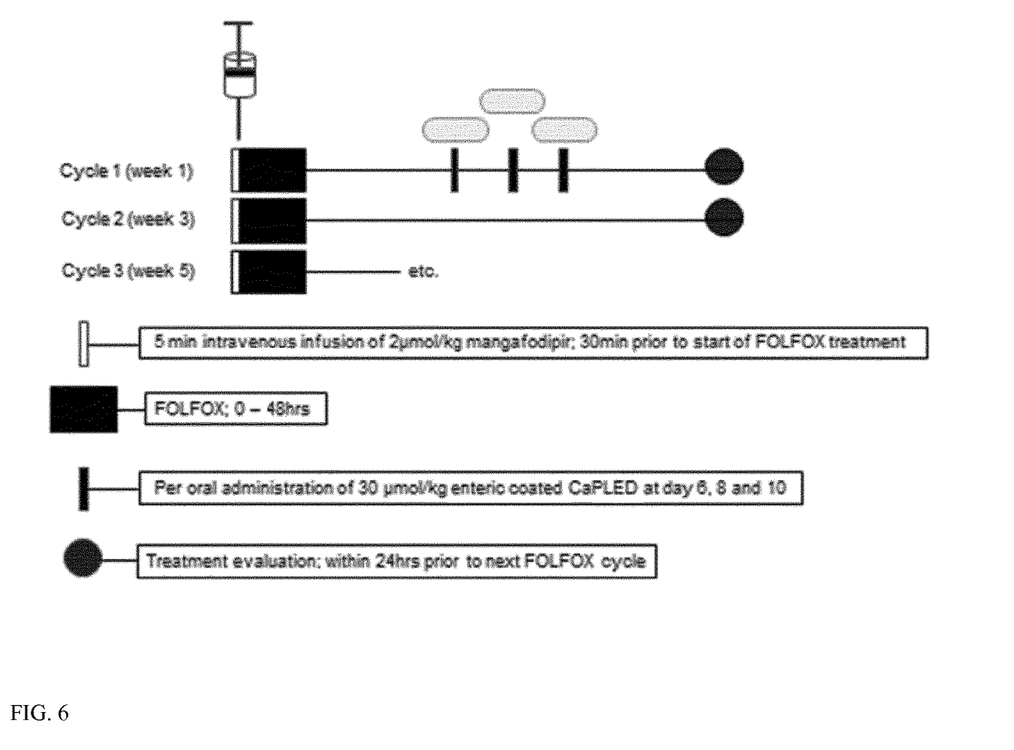
FIG. 6 shows an intendent example how the present invention can be used in a patient with CRC by per oral administration of enteric coated CaPLED on each of day 6, 8 and 10 of the FOLFOX cycle, separately or in combination with pre-treatment with intravenous infusion of mangafodipir. When it comes to enteric coated CaPLED, the present treatment schedule offers an attractive possibility to chelate and increase the excretion of accumulated neurotoxic Pt and hence lowering the serious problem of oxaliplatin-associated dose-limiting PSN. Anticipating 50% bioavailability, a reasonable per oral dose would be 30 µmol/kg per treatment day.

Inhibitory effects of oxaliplatin on the anticancer activity of fodipir have not been recognized before, although results were published already in 2012 which today in the light of new knowledge actually indicate such an inhibition. The inventors Karlsson and Andersson (Karlsson et al., 2012B) originally interpreted the current experiments, as follows: "Oxaliplatin killed CT26 cells in a concentration-dependent manner (FIG. 6 in the article). Neither 10, 30, nor 100 μM fodipir interfered negatively with the cancer cell killing ability of oxaliplatin. An additive effect of 10 μM fodipir was seen in the lower concentration range of oxaliplatin". This is a correct interpretation when it comes to oxaliplatin alone and in combination with 10 μM fodipir but Karlsson, Andersson and the co-authors oversaw the inhibitory effect of 100 μM (and 30 μM) oxaliplatin on the cancer cell killing activity of fodipir. However, the surprising finding by Coriat et al., 2014 showing a curative effect of mangafodipir has specified and updated this particular aspect.

As shown in Example 1, fodipir at a concentration of 100 μM possesses an almost complete cell killing activity towards CT26 colon cancer cells. Adding increasing concentration of oxaliplatin, from 0.1 μM to 30 μM, in the presence of 100 μM fodipir, causes a successively lower cancer cell killing activity. The antagonist activity of oxaliplatin disappeared at 100 μM. In classical pharmacology such an effect of oxaliplatin is known as a partial agonistic effect. However, it is far from an easy task to explain how such an interaction between oxaliplatin and fodipir takes place. It is known that the cancer cell killing activity of fodipir disappears in the presence of metals that bind to fodipir. Metals with high binding affinity, such as $Zn^{2+}$, are more effective inhibitors than metals with lower binding affinity, such as $Mn^{2+}$ (Karlsson et al., 2012B). One plausible explanation to the antagonistic effect of oxaliplatin towards fodipir may be that $Pt^{2+}$ binds to fodipir. However, there are no published data showing that $Pt^{2+}$ binds to fodipir or to its metabolites DPMP and PLED.

The protective effect of MnPLED-derivatives against oxaliplatin-induced PSN is anticipated to depend on the intact Mn-complex, according to prior art (U.S. Pat. No. 9,187,509; Yri et al., 2009; Coriat et al., 2014). However, reinterpreting old data (Karlsson et al., 2012B) and anticipating binding of $Pt^{2+}$ to fodipir (or its metabolites), as described in Example 1, reveal new and very exciting and novel possibilities to treat oxaliplatin-induced PSN.

Mangafodipir was originally developed as an MRI contrast agent (see Karlsson et al., 2015). When an MRI dose (i.e., 5-10 μmol/kg) is injected into humans or rats about 80% of its manganese(II) ($Mn^{2+}$) is released from fodipir or its metabolites, and only 20% stays bound. Release of paramagnetic $Mn^{2+}$ is in fact a prerequisite for the diagnostic contrast enhancing properties (Wendland, NMR Biomed. 2004; 17:581-594). The MnSOD mimetic activity, on the other hand, fully depends on the intact manganese complex, i.e., neither fodipir nor $Mn^{2+}$ alone possesses any such activity (Brurok et al., 1999). In the MnSOD reaction, redox active $Mn^{2+}$ is first oxidized by $O_2^-$ (superoxide) to $Mn^{3+}$. The $Mn^{3+}$ thus formed is subsequently reduced to $Mn^{2+}$ by a second $O_2^-$, making this reaction a true metal-catalyzed dismutation like that catalysed by the transition manganese, copper or iron-containing SOD enzymes.

The main amount of intravenously administered oxaliplatin undergoes rapid and extensive non-enzymatic biotransformation (Graham et al. Clin Cancer Res 2000; 6:1205-2018) and forms a variety of reactive intermediates in blood and plasma. Up to 17 platinum-containing metabolites have been detected in plasma ultrafiltrate samples from patients. These metabolites (except for the dichloro/monoaquamonochloro complex) are not considered to possess tumoricidal activity, to any larger extent. It is commonly accepted for platinum drugs that DNA damage is largely responsible for their tumoricidal properties (Raymond et al. Molecular Cancer Therapeutics 2002; 1:227-235). It is furthermore considered unlikely that the active metabolite, i.e., the Pt(II)-$Cl_2$ complex of oxaliplatin, contributes to the PSN to any larger extent, since only a limited amount (<3%) of oxaliplatin undergoes biotransformation into the Pt(II)-$Cl_2$ complex (Shord et al. Anticancer Res. 2002; 22:2301-2309).

Similarly to cisplatin (another Pt(II)-Cl2, the main mechanism of action of oxaliplatin is mediated through the formation of DNA adducts (Raymond et al. Annal of Oncology. 1998; 9:1053-1071).When the Pt(II)-compound enters the cell, one chloride ligand dissociates to form a reactive monoaquamonochloro complex, which reacts rapidly with guanines on the DNA to form monoadducts. The subsequent dissociation of the second chloride ligand allows the conversion of the transiently formed mono-adducts to a variety of stable di-adducts. These intrastrand adducts effectively block both DNA replication and transcription, and are considered the major cytotoxic lesions. The elimination of $Pt^{2+}$ occurs mainly in urine rather than in feces (Graham et al., 2000). A mass balance study was performed to determine the major route of platinum elimination in patients after a single dose of oxaliplatin. Over a 5-day period, 53.8% of the Pt dose was excreted in the urine and only 2.1% in feces. That means that only about half of the given Pt dose was eliminated from the body over a 5-day period. This amount was only marginally increased in an 11-day period study.

It is unclear why cisplatin but not oxaliplatin is highly nephrotoxic. It is neither clear why cisplatin but not oxaliplatin causes ototoxicity. Although cisplatin causes PSN, its toxicological profile differs from that of oxaliplatin, for poorly known reasons. There are, however, some distinct differences in pharmacokinetic properties between cisplatin and oxaliplatin that might explain the different toxic profiles of these two compounds.

Oxaliplatin has a large volume of distribution, about 600 litres, compared to about 20 litres for cisplatin (Graham et al., 2000). This difference implies a much higher lipophilicity of oxaliplatin compared to cisplatin. This may in turn implies a much higher cell membrane permeability and cellular retention of the former. Unlike cisplatin, oxaliplatin accumulates $Pt^{2+}$ in red blood cells (RBC) with a terminal Pt half-life of about 50 days, more or less identical to that of RBC (Gamelin et al. Clin Cancer Res. 1997; 3:891-899), which indicates irreversible accumulation. $Pt^{2+}$ seems to be trapped in RBC through covalent binding to globin.

Metabolites of cisplatin, as well as those of oxaliplatin, react with small proteins with sulfhydryl groups, such as glutathione, cysteine and methionine, and then with high molecular weight proteins through covalent links (Boisdron-Celle et al. Bull Cancer. 2001; 88 Spec No:S14-19). Thus, their terminal half-lives are long. Pt-accumulation in plasma occurs after cisplatin administration but not to any greater extent after oxaliplatin administration. This difference may also help to explain the different toxicological profiles of the two drugs.

Although Pt(II)-based drugs as cancer chemotherapeutic agents have been widely studied, the exact knowledge of mechanisms governing their accumulation in cells is still lacking. Over several years, Cu transporters have been proposed to be involved in cellular import and export of Pt(II) chemotherapeutic agents, as well as in their resistance mechanisms (Spreckelmeyer et al. Molecules 2014; 19:15584-15610). Expression of the human Cu transporter 1 (hCtr 1) results in increased sensitivity to cisplatin, whereas expression of two Cu(I) proteins exporting ATPase, i.e., ATP7A and ATP7B, is involved in the resistance to cisplatin, either by sequestering drug away from its targets (ATP7A), or by exporting the drug from the cell (ATP7B). However, oxaliplatin differs from cisplatin in that its dependence on hCtr1 diminishes at higher concentrations. This may suggest a higher degree of passive diffusion of oxaliplatin, due to its higher lipophilicity than cisplatin.

Yokoo et al. (Biochem Pharmacol. 2007; 74:477-487) reported a much higher accumulation of $Pt^{2+}$ in rat kidneys after cisplatin administration in comparison to that of oxaliplatin. This difference presumably explains the higher nephrotoxic potential of the former.

Recent studies in animal models suggest a role of transport mechanisms in platinum-induced neurotoxicity. Sprowl et al., Proc Natl Acad Sci USA. 2013; 110:11199-11204) reported that accumulation of oxaliplatin in, and damage to, neuronal cells was linked to the organic cation transporter 2 (OCT2), a protein expressed in the neurons of the dorsal root ganglia. Overexpression of OCT2 resulted in a significant (up to 35-fold) increase in neuronal uptake of oxaliplatin, while OCT2 gene knockout protected against the development of peripheral neurotoxicity.

To summarize, the above described distinct difference in toxicological profiles between cisplatin and oxaliplatin, with respect to nephrotoxicity, PNS and ototoxicity, is presumably due to differences in uptake and cellular retention of these drugs and their Pt-metabolites.

Metal complexes of fodipir (or its metabolites) are excreted through the kidneys by a GFR-governed process (Toft et al., 1997), i.e., through of a very efficacious process. The PKs of Pt-metabolites in plasma is typically triphasic in man, characterized by a short initial distribution phase and a long terminal elimination phase with a half-life of about 11 days. The long terminal half-life probably represents a slow release of low molecular weight platinum-amino acid conjugates after degradation of cellular macromolecules (Graham et al., 2000). The slow release of Pt-amino acid conjugates may explain the curative efficacy of mangafodipir. It seems plausible that fodipir (or its metabolites) may increase $Pt^{2+}$-elimination during the long elimination phase by having high enough affinity for $Pt^{2+}$ (or other oxidation stages) for partially or fully replacing $Mn^{2+}$, which in turn may increase renal excretion of $Pt^{2+}$ substantially. Such a process may explain the highly surprisingly curative effect of mangafodipir on preexisting PNS, as revealed in the work of Coriat et al., 2014, and maybe in the NCT01619423 study conducted by PledPharma AB.

From the above description it seems reasonable to propose that toxic side-effects, e.g., neurotoxicity caused by oxaliplatin is mainly due to retention of Pt-metabolites (other than the tumoricidal $Pt(II)$-$Cl_2$ one) and irreversible binding of $Pt^{2+}$ to proteins in normal cells. Theoretically, one option to lower the side-effects of oxaliplatin would thus be to find ways of lowering retention of Pt-metabolites in normal cells but without interfering negatively with the tumoricidal efficacy of these drugs. Taking in consideration the very high degree of body retention of $Pt^{2+}$ after administration of oxaliplatin, a reasonable way would be to "selectively" increase excretion of the "non-active" Pt fraction. For obvious reasons, such an approach is far from a straight forward one.

As illustrated in Example 2, mangafodipir and fodipir when administered close to oxaliplatin, increases renal Pt-excretion by 8.0% and 40.6%, respectively, which in turn may explain why mangafodipir prevent and cure oxaliplatin-induced PSN, as described by Coriat et al., 2014.

The finding that fodipir increased Pt-excretion more than mangafodipir is rather expected, as a "naked" chelator is expected to bind $Pt^2$ more readily than one already occupied with a transitional metal. Due to the high lipophilicity of oxaliplatin (distribution volume of about 600 litre), $Pt^{2+}$ is expected to disappear rather rapidly from the water compartment and to large extent escape a water soluble chelator such as fodipir. From this view, the increase in renal excretion of $Pt^{2+}$ in the presence of fodipir is highly promising. During the long elimination phase where $Pt^{2+}$-protein adducts are broken down (Graham et al., 2000), $Pt^{2+}$ may in fact be more readily available for fodipir. Which in turn may result in even more profound effect on renal excretion of $Pt^{2+}$ and PSN, in particular when fodipir or other PLED-derivatives are administered repeatable over time. Nevertheless, the present invention suggests, in opposite to prior art (Yri et al., 2009; Coriat et al., 2014; U.S. Pat. No. 9,187,509), that the ability of mangafodipir to protect against PNS is not a property of the intact Mn-complex but a property of fodipir alone or its metabolites (DPMP and PLED). The invention, furthermore, suggests that this effect is due the ability of fodipir (or its metabolites) to bind $Pt^{2+}$ and excrete it through the kidney, and hence lower the accumulated amount.

Chemotherapy-induced PSN occurs with chemotherapeutics across drug classes with distinctly different anti-tumour mechanisms, such as taxanes and platinum compound. Despite potentially diverse mechanisms underlying the development of PSN, common degenerative pathways may be triggered when the normal processes and energy delivery mechanisms of the peripheral nervous system become disrupted. Experimental studies suggest that the underlying mechanism in the development of these neuropathies is oxidative stress and subsequent mitochondrial toxicity in primary nerve sensory axons arising from reduced mitochondrial bioenergetics, e.g., adenosine triphosphate (ATP) production (see Karlsson et al., 2017). In the case of oxaliplatin-induced PSN, it seems reasonable to postulate intracellular accumulation of $Pt^{2+}$ as the causative to detrimental oxidative stress and subsequent cell death. Both clinical and preclinical data suggest that the MnSOD mimetic mangafodipir is an efficacious compound in PSN treatment. However, taken in consideration that mangafodipir and its manganese-metabolites are eliminated within hours after administration, increasing the MnSOD activity intermittently with mangafodipir is not expected to have any major curative effect. According to the present invention chelation of $Pt^{2+}$ to fodipir or its metabolites and subsequent renal elimination is a more plausible explanation. This gives a number of advantages such as that manganese can be excluded which was previously thought to be essential.

Oxaliplatin and cisplatin are square planar metal complexes, where Pt(II) binds to two bidentate ligands in the case of oxaliplatin, and two monodendate ligands in the case of cisplatin. The affinity between $Pt^{2+}$ and DPDP, or its metabolites DPMP and PLED, is not known. Taking in consideration prior art showing no negative influence of mangafodipir on the tumoricidal activity of oxaliplatin (Laurent et al., 2005; Alexandre et al., 2006; Karlsson et al., 2017), the present finding that it is possible to "selectively" increase renal excretion of "non-active" $Pt^{2-}$, without interfering with the "active" fraction, is apparently a surprising one. Nevertheless, the present invention solves the serious problem of oxaliplatin-induced PNS (and other Pt-induced side effects). Furthermore, as this can be achieved with the chelator fodipir (DPDP) or its metabolites (DPMP and PLED) alone, literally eliminates the problem of manganese-induced neurotoxicity. Furthermore the present invention opens for much more efficacious treatment schedules, where fodipir or its derivatives can be administrated both temporally and spatially separated from chemotherapy. And most important, fodipir or a derivative of it can be administered far more frequent than mangafodipir and calmangafodipir.

Figure 5:
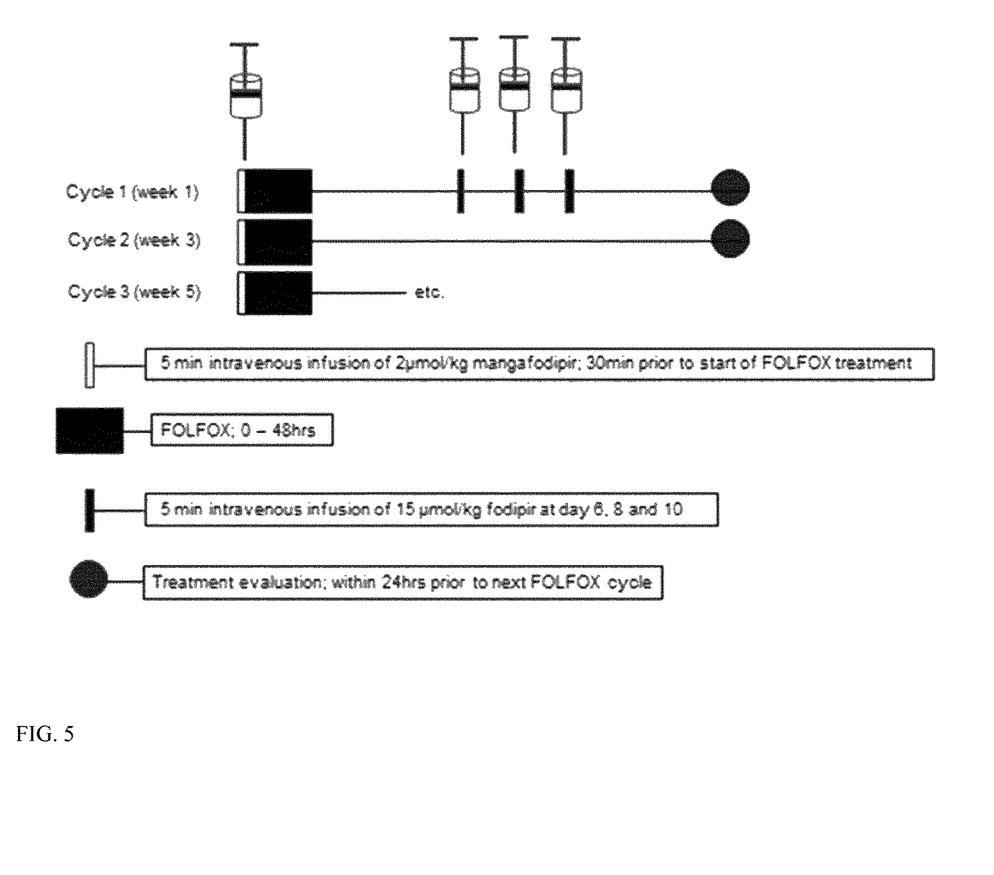
FIG. 5 shows an intendent example how the present invention can be used in a patient with CRC by intravenous infusion of 15 µmol/kg fodipir on each of day 6, 8 and 10 of the FOLFOX cycle, separately or in combination with pre-treatment with intravenous infusion of mangafodipir, alternatively calmangafodipir, on day 1. When it comes to fodipir, the present treatment schedule offers an attractive possibility to chelate and increase the excretion of accumulated neurotoxic Pt and hence lowering the serious problem of oxaliplatin-associated dose-limiting PSN.

Examples 3 and 4 illustrates two of several possible treatment schedules making use of intravenously administered fodipir, separately or in combination with mangafodipir (FIGS. 5 and 6). Use of mangafodipir or calmangafodipir to reduce dose-limiting toxicities that is associated to the acute FOLFOX-induced oxidative stress, such as leukocytopenia, as demonstrated by Karlsson et al., 2012A and 2012B in both human patients and in mice, may be motivated. However, the benefits have to be carefully considered from the manganese toxicity potential of these compounds.

EXAMPLE 1

This example reinterprets previous published data (Karlsson et al., 2012B). Karlsson et al. Transl Oncol. 2012B; 5:492-502 is hereby incorporated herein by reference in its entirety.

Another highly important but until now unrecognized aspect of combining fodipir and oxaliplatin is that the latter inhibits the anticancer effect of the former (Karlsson et al., 2012B), as schematically illustrated in this Example 1).

Original Interpretation

The inventors Karlsson and Andersson (Karlsson et al., 2012B) interpreted the current experiments, as follows: "Oxaliplatin killed CT26 cells in a concentration-dependent manner (FIG. 6). Neither 10, 30, nor 100 µM fodipir interfered negatively with the cancer cell killing ability of oxaliplatin. An additive effect of 10 µM fodipir was seen in the lower concentration range of oxaliplatin". This is a correct interpretation when it comes to oxaliplatin alone and in combination with 10 µM fodipir but Karlsson, Andersson and the co-authors oversaw the inhibitory effect of 100 µM (and 30 µM) oxaliplatin on the cancer cell killing activity of fodipir. However, the surprising finding by Coriat et al., 2014 showing a curative effect of mangafodipir has specified and updated this particular aspect.

New Interpretation

Figure 1:
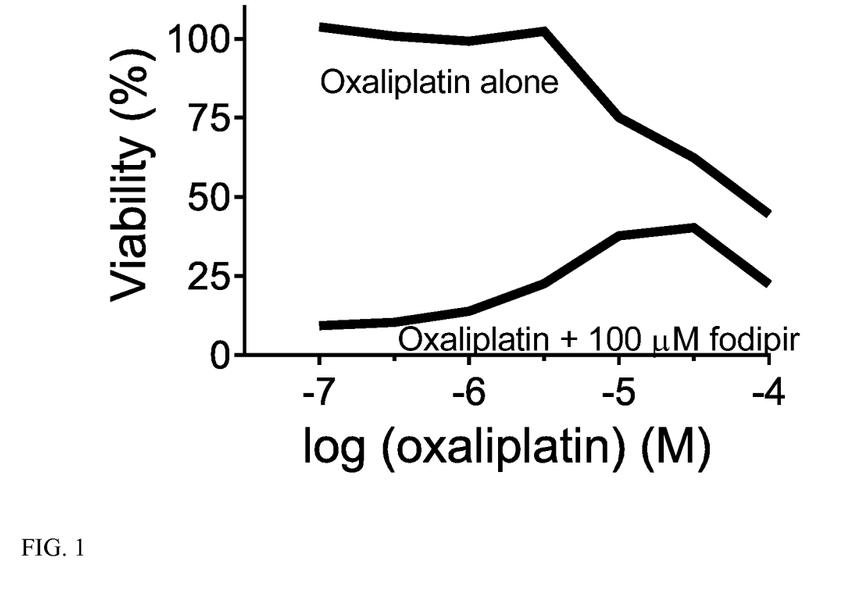
FIG. 1 illustrates schematically the cancer cell killing activity of fodipir in colon cancer cells (CT26), seen as a decrease in Cell Viability, as described in Example 1.
Figure 2:
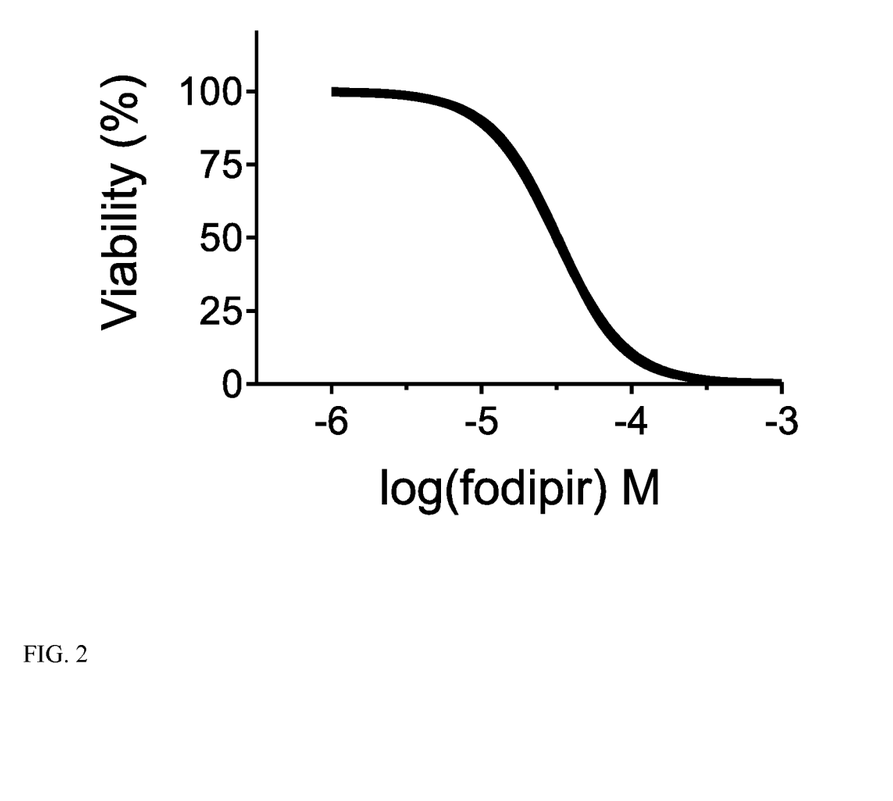
FIG. 2 illustrates schematically the cancer cell killing activity of oxaliplatin, in the absence and presence of various concentrations of fodipir in colon cancer cells (CT26), seen as a decrease in Viability, as described in Example 1.

As schematically shown in FIG. 1, fodipir at a concentration of 100 µM possesses an almost complete cell killing activity towards CT26 colon cancer cells. Adding increasing concentration of oxaliplatin, from 0.1 µM to 30 µM, in the presence of 100 µM fodipir, causes a successively lower cancer cell killing effect (FIG. 2). The antagonist activity of oxaliplatin disappeared at 100 µM. In classical pharmacology such an effect of oxaliplatin is known as a partial antagonistic/agonistic effect. Karlsson et al., 2012B describes that the cancer cell killing activity of fodipir disappears in the present of metals that binds to fodipir. Metals with high binding affinity, such as $Zn^{2+}$, with a log formation constant (log $K_{ML}$) of 18 are more effective inhibitors than metals with lower binding affinity, such as $Mn^{2+}$ with a log $K_{ML}$ of 15 (Karlsson et al., 2012B). $Ca^{2+}$ having a low binding affinity for fodipir (log $K_{ML}$=9), which is about one million times lower than that of $Mn^{2+}$, does not display any inhibitory effect on oxaliplatins's cancer cell killing activity, as shown by Karlsson et al., 2012B.

An attractive and plausible explanation to the antagonistic effect of oxaliplatin towards fodipir may be that $Pt^{2+}$ binds to fodipir.

EXAMPLE 2

This example measured platinum (Pt) urine excretion in animals receiving 2 mg/kg oxaliplatin intravenously (i.v.), following i.v. injection of mangafodipir (20 mg/kg), fodipir (17.4 mg/kg) or saline (control).

Method 2 male Wistar rats (approximately 250 g) were injected i.v., via one of the tail veins, with 0.25 ml mangafodipir (20 mg/kg; Lot no. 303001, Nycomed Imaging AS) or fodipir (17.4 mg/kg; Lot no. PKJ 1285/113-14, Nycomed Imaging AS), each corresponding to 26.4 µmol/kg. Another control rat received saline instead of mangafodipir or fodipir. Five minutes later, all animals received 0.25 ml oxaliplatin (2 mg/ml; diluted in 5% glucose) i.v., corresponding to 2 mg/kg. The rats were then immediately placed in metabolic cages for urine collection over a period of 0-24 hours. The urine samples were thereafter stored at −80° C. until Pt analysis. Before analysis, the samples were thawed and extensively shaken to obtain homogenous samples. A five ml aliquot was taken from each sample and 5 ml concentrated nitric acid was added. The samples were then resolved in a microwave oven and thereafter diluted with distilled water. The Pt content of each sample was analyzed by ICP-MS (Inductively Coupled Plasma Mass Spectrometry). An identical sample of oxaliplatin as that injected in the rats (i.e., 0.25 ml) were withdrawn and injected into the test tubes. This sample was treated in an identical manner to that of the urine samples and analyzed for its Pt content. Results are presented as total 0-24 h urine Pt content, expressed as the total amount, as well as, as percentage of the injected dose.

Results

Figure 3:
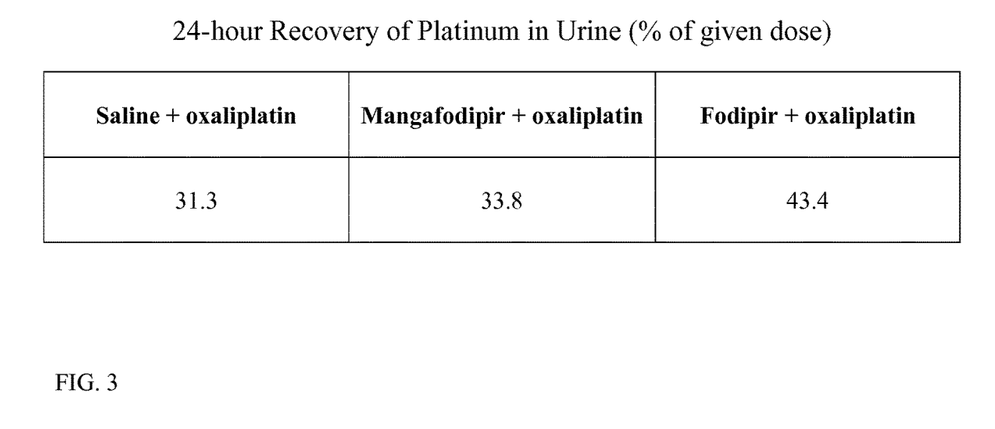
FIG. 3 shows the 0-24 h recovery of platinum in urine (% of given dose) in rats after intravenously administered oxaliplatin (2 mg/kg), intravenously co-administered with saline (control), mangafodipir (26.4 µmol/kg) or fodipir (26.4 µmol/g)
Figure 4:
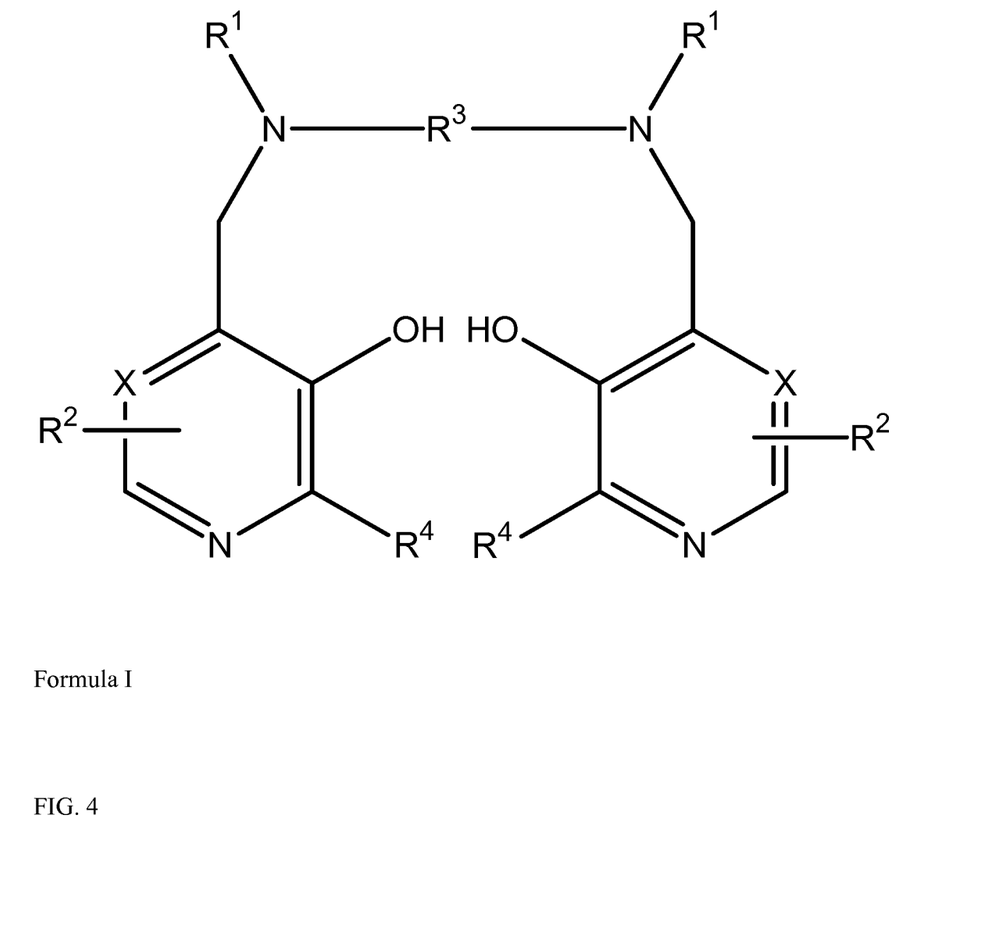
FIG. 4 shows formula I, the meaning of the various groups is explained in the description.

Twenty-four hours after i.v. injection of 0.25 ml mangafodipir (26.4 μmol/ml) or fodipir (26.4 μmol/ml) or a corresponding volume of saline, followed by i.v. injection of 0.25 ml 2 mg/ml oxaliplatin, the recovery of oxaliplatin-derived Pt in urine in saline treated animals was 86.84 μg, corresponding to 31.3% of the administered dose of oxaliplatin-derived Pt (277.5 μg). The corresponding recoveries in animals treated with mangafodipir or fodipir, were increased to 93.72 μg and 120.36 μg, respectively, corresponding to 33.8% and 43.4%, respectively (FIG. 3). These recoveries correspond to 8.0% and 40.6% increase in Pt-excretion, respectively.

Conclusion

Pretreatment with mangafodipir or fodipir both increases renal excretion of Pt and consequently lowers Pt accumulation in the body, which in turn presumably reduces serious side effects of oxaliplatin, in particular PSN. The finding that fodipir was more efficacious than mangafodipir in this particular sense is expected, as a non-metal coordinated compound, such as fodipir, is expected to bind "competing" $Pt^{2+}$ more readily than a metal-coordinated compound, such as mangafodipir. However, the difference between fodipir and mangafodipir is most probably exaggerated in the used model where only early effects of these compounds on $Pt^{2+}$ excretion, after oxaliplatin administration, were studied. Due to its high lipophilicity, oxaliplatin disappears rapidly from the extracellular water compartment and $Pt^{2+}$ will hence escape chelator-facilitated renal excretion to a large extent. The situation during the terminal elimination phase with a half-life of more than 10 days, might be quite more advantageous.

EXAMPLES 3 and 4

These two Examples illustrates two out of many possible treatment schedules of the present invention, as described more in detailed in the legends of FIGS. 5 and 6.

The invention claimed is:

1. A method for the treatment of a chemotherapy drug induced peripheral sensory neuropathy in a patient undergoing chemotherapy, wherein the chemotherapy drug comprises platinum ions, the method comprising administering to the patient an effective amount of a platinum ion chelating dipyridoxyl compound according to Formula I, or a pharmaceutically acceptable salt thereof, wherein the dipyridoxyl compound is coordinated with a metal ion which is not a transition metal or uncoordinated, Formula I wherein
X represents CH or N,
each $R^1$ independently represents hydrogen or —$CH_2COR^5$;
$R^5$ represents hydroxy, optionally hydroxylated alkoxy, amino or alkylamido;
each $R^2$ independently represents $ZYR^6$ wherein Z represents a bond or a $C_{1-3}$ alkylene or oxoalkylene group, optionally substituted by $R^7$;
Y represents a bond, an oxygen atom or $NR^6$;
$R^6$ is a hydrogen atom, $COOR^8$, alkyl, alkenyl, cycloalkyl, aryl or aralkyl group, optionally substituted by one or more groups selected from $COOR^8$, $CONR^8_2$, $NR^8_2$, $OR^8$, =$NR^8$, =O, OP(O) $(OR^8)R^7$ and $OSO_3M$;
$R^7$ is hydroxy, optionally hydroxylated, optionally alkoxylated alkyl or aminoalkyl group;
$R^8$ is a hydrogen atom or an optionally hydroxylated, optionally alkoxylated alkyl group;
M is a hydrogen atom;
$R^3$ represents a $C_{1-8}$ alkylene, a 1,2-cykloalkylene, or a 1,2-arylene group, optionally substituted with $R^7$; and
each $R^4$ independently represents hydrogen or $C_{1-3}$ alkyl.

2. The method according to claim 1, wherein the chemotherapy drug comprises oxaliplatin.

3. The method according to claim 1, wherein the metal which is not a transition metal comprises at least one selected from the group consisting of calcium and magnesium.

4. The method according to claim 1, comprising administering about 1 to 100 μmol/kg body weight of the compound.

5. The method according to claim 1, comprising administering about 5 to 50 μmol/kg body weight of the compound.

6. The method according to claim 1, comprising administering about 5 to 30 μmol/kg body weight of the compound.

7. The method according to claim 1, wherein $R^5$ is hydroxy, $C_{1-8}$ alkoxy, ethylene glycol, glycerol, amino or $C_{1-8}$ alkylamido; Z is a bond or a group selected from $CH_2$, $(CH_2)_2$, CO, $CH_2CO$, $CH_2CH_2CO$ and $CH_2COCH_2$; Y is a bond; $R^6$ is a mono- or poly(hydroxy or alkoxylated) alkyl group or of the formula OP(O) $(OR^8)R^7$; and $R^7$ is hydroxy, or an unsubstituted alkyl or aminoalkyl group.

8. The method according to claim 1, wherein $R^3$ is ethylene and each group $R^1$ represents —$CH_2COR^5$ in which $R^5$ is hydroxy.

9. The method according to claim 1, wherein the compound of Formula I is one selected from the group consisting of N,N'-bis-(pyridoxal-5-phosphate)-ethylenediamine-N,N'-diacetic acid (DPDP; fodipir), N,N'-dipyridoxyl ethylenediamine-N,N'-diacetic acid (PLED), and a pharmaceutically acceptable salt thereof.

10. The method according to claim 1, wherein the compound of Formula I is N,N'-bis-(pyridoxal-5-phosphate)-ethylenediamine-N,N'-diacetic acid (DPDP; fodipir) or a pharmaceutically acceptable salt thereof.

11. The method according to claim 1, wherein the chemotherapy drug comprises oxaliplatin.

* * * * *